United States Patent [19]

Miyazaki et al.

[11] Patent Number: 4,647,551

[45] Date of Patent: * Mar. 3, 1987

[54] FOR PRODUCING ETHYLENE GLYCOL AND/OR A GLYCOLIC ACID ESTER, CATALYST COMPOSITION AND PROCESS FOR PRODUCING THE CATALYST COMPOSITION

[75] Inventors: Haruhiko Miyazaki; Koichi Hirai; Taizo Uda; Yasuo Nakamura, all of Ube; Harumi Ikezawa, Onoda; Takanori Tsuchie, Ube, all of Japan

[73] Assignee: Ube Industries, Ltd., Yamaguchi, Japan

[*] Notice: The portion of the term of this patent subsequent to Apr. 3, 2001 has been disclaimed.

[21] Appl. No.: 496,997

[22] Filed: May 23, 1983

[30] Foreign Application Priority Data

May 28, 1982 [JP] Japan ................... 57-89985

[51] Int. Cl.$^4$ ................................ B01J 21/08
[52] U.S. Cl. .................... 502/200; 502/244
[58] Field of Search ................. 502/244, 200

[56] References Cited

U.S. PATENT DOCUMENTS

| | | | |
|---|---|---|---|
| 1,726,170 | 8/1929 | Britton et al. | 502/200 X |
| 1,956,585 | 5/1934 | Oglesby et al. | 502/244 X |
| 2,289,924 | 7/1942 | Morrell et al. | 502/200 X |
| 2,783,286 | 2/1957 | Reynolds | 502/244 X |
| 2,891,094 | 6/1959 | Karkalits, Jr. et al. | 502/244 X |
| 3,803,055 | 4/1974 | Reich | 502/244 |
| 4,112,245 | 9/1978 | Zehner et al. | 568/864 |
| 4,440,873 | 4/1984 | Miyazaki et al. | 502/244 |

FOREIGN PATENT DOCUMENTS

| | | | |
|---|---|---|---|
| 0545045 | 8/1957 | Canada | 502/233 |
| 0137194 | 7/1977 | German Democratic Rep. | 502/200 |
| 5253806 | 10/1975 | Japan | 502/244 |
| 57-122946 | 7/1982 | Japan | 502/200 |
| 0454925 | 3/1975 | U.S.S.R. | 502/200 |
| 0733720 | 7/1977 | U.S.S.R. | 502/200 |

Primary Examiner—Andrew H. Metz
Assistant Examiner—William G. Wright

[57] ABSTRACT

A hydrogenation catalyst composition useful for the hydrogenation of an oxalate diester, said composition being composed of a reduction product of a copper-containing silica gel formed by contacting an amine complex of copper with silica gel having an average particle diameter of not more than 200$\mu$ and a process for producing the aforesaid composition. Using a catalyst composed of the aforesaid composition, ethylene glycol and/or a glycolic acid ester can be produced from an oxalate diester efficiently with high conversions and selectivities and without causing pollution attributed to the use of a chromium-containing catalyst composition.

5 Claims, No Drawings

FOR PRODUCING ETHYLENE GLYCOL AND/OR A GLYCOLIC ACID ESTER, CATALYST COMPOSITION AND PROCESS FOR PRODUCING THE CATALYST COMPOSITION

This invention relates to a commercial process for producing ethylene glycol and/or a glycolic acid ester from an oxalate diester efficiently with high conversions and selectivities and without causing pollution attributed to the use of a chromium-containing catalyst composition. The invention also relates to a catalyst composition for use in the aforesaid process, and to a process for producing the catalyst composition.

More specifically, this invention relates to a hydrogenation catalyst composition for use in the hydrogenation of an oxalate diester, composed of a reduction product of copper-containing silica gel formed by contacting an ammine complex of copper with silica gel having an average particle diameter of not more than $200\mu$. This catalyst composition is prepared by contacting an ammine complex of copper with silica gel having an average particle diameter of not more than $200\mu$ in the presence of an aqueous medium to form copper-containing silica gel, and subjecting the copper-containing silica gel to reduction. The invention also pertains to a process for producing ethylene glycol and/or a glycolic acid ester, which comprises hydrogenating an oxalate diester in the gaseous or vapor phase at an elevated temperature in the presence of the aforesaid catalyst composition.

It is known to prepare ethylene glycol and/or a glycolic acid ester by the catalytic hydrogenation of an oxalate diester in the gaseous or vapor phase at an elevated temperature in the presence of a hydrogenation catalyst, and a Cu/Cr type catalyst has already been proposed as the hydrogenation catalyst (see Japanese Patent Publication No. 42971/1980 corresponding to U.S. Pat. No. 4,112,245; and German Pat. No. 459,603).

Cu/Cr type catalysts are generally known as catalysts which can be utilized to hydrogenate esters to the corresponding alcohols. In practice, however, the use of this type of Cr-containing catalysts causes problems. It is extremely difficult, if not impossible by a complicated and expensive operation, to recover chromium efficiently and completely from a spent Cu/Cr type catalyst, and such a catalyst is not suitable for industrial operations. Since chromium, even in trace, exhibits strong toxicity to humans, discarding of chromium-containing catalyst residues in general environments should be avoided. This leads to the defect that the high catalytic activity of the Cu/Cr type catalysts is reduced in practice because of the difficulty of disposing of the spent catalysts.

It is generally known that various other metals or metal compounds can be used as hydrogenation catalysts or their components. Examples include Raney nickel, nickel, cobalt, copper, iron, platinum, and palladium, and their oxides and sulfides. It is well known that these generally known metals or metal compounds are not necessarily useful in any catalytic hydrogenation reactions, and a desired hydrogenation reaction cannot be carried out efficiency unless a catalyst suitable for the desired hydrogenation is selected according to the mode of the reaction, the hydrogenation reaction conditions, etc. It is also widely known that no established guideline exists for selecting such a suitable catalyst.

We have extensively worked in order to develop a catalyst composition for the catalytic hydrogenation of an oxalate diester, which is free from chromium and has a better catalytic activity than that of conventional catalysts for the catalytic hydrogenation of an oxalate diester.

Consequently, we have found that a catalyst composition composed of a reduction product of copper-containing silica gel formed by contacting an ammine complex of copper with silica gel having an average particle diameter of not more than $200\mu$ is useful for forming ethylene glycol and/or a glycolic acid ester efficiently from an oxalate diester in higher conversions and selectivities with industrial advantage than the known Cu-Cr catalysts and can overcome the trouble of conventional chromium-containing catalyst compositions. It has also been found that this catalyst composition can be prepared by contacting an ammine complex of copper with silica gel having an average particle diameter of not more than 200 to form copper-containing silica gel, and subjecting the resultant copper-containing silica gel to reduction.

It is an object of this invention therefore to provide a hydrogenation catalyst composition for the hydrogenation of an oxalate diester.

A second object of this invention is to provide a process for producing the aforesaid hydrogenation catalyst.

A third object of this invention is to provide a process for producing ethylene glycol and/or a glycolic acid ester from an oxalate diester in the presence of the aforesaid hydrogenation catalyst.

The above and other objects and advantages of this invention will become more apparent from the following description.

The hydrogenation catalyst composition of this invention can be produced by a process which comprises contacting an ammine complex of copper with silica gel having an average particle diameter of not more than $200\mu$, and subjecting the resulting copper-containing silica gel to reduction. According to its one embodiment, an aqueous solution containing an ammine complex of copper is mixed with silica gel having an average particle diameter of not more than $200\mu$. The resultant copper-containing silica gel is subjected to a reducing treatment in the presence of hydrogen gas.

The aqueous solution containing an ammine complex of copper can be prepared by a method known per se. For example, it can be prepared by adding ammonia to an aqueous solution containing a copper ion until the solution becomes alkaline. It can also be prepared by adding copper flakes to a concentrated aqueous solution of ammonia and passing air through the mixture.

The aqueous solution containing a copper ion can be obtained by dissolving a water-soluble copper compound (including copper salts) in water. Examples of such copper compounds are copper nitrate, copper sulfate, copper oxalate, copper chloride, copper carbonate, and copper acetate. Cupric nitrate is especially preferred.

The silica gel is commercially available, and commercial silica gel having an average particle diameter of not more than 200 microns or adjusted to this particle size range can be used in this invention. It can be prepared by known methods which include, for example, dry methods such as the decomposition of a silicon halide or an organic silicon compound, or reduction of silica sand with coke by heating in arc followed by oxidizing the resulting vapor, and a wet method comprising decomposition of sodium silicate with an acid.

The silica gel used in the catalyst preparation in accordance with this invention should be in the form of fine particles having an average particle diameter of not more than 200 microns. When silica gel having an average particle diameter of more than $200\mu$ is used, the amount of copper deposited on silica gel becomes small, and the resulting catalyst has much lowered activity. There is no particular lower limit to the average particle diameter of silica gel. But preferably, it is down to about $1 \, m\mu$. The especially preferred average particle diameter is about $5 \, m\mu$ to about $150\mu$.

According to one example of the aforesaid embodiment, the catalyst composition of this invention can be produced by the following procedure.

Such a water-soluble copper compound as exemplified above, for example cupric nitrate, is dissolved in water, and conc. aqueous ammonia is added to the resulting aqueous solution containing a cupric ion until the pH of the mixture reaches at least about 10, for example about 10 to about 12. Thus, a deep blue aqueous solution forms. Silica gel having an average particle diameter of not more than $200\mu$ is added to the deep blue aqueous solution, and they are stirred to mix and contact them fully with each other. The mixing can be effected either at room temperature or at elevated temperatures, for example at room temperature to about 150° C., under atmospheric or elevated pressures. Elevated temperatures, for example about 40° to about 100° C., are preferred. The resulting product is subjected, for example, to an evaporating treatment to form a solid residue. As a result, a copper ion is supported on the silica gel to form copper-containing silica gel. The resulting solid residue is then washed fully with water and dried. The dried residue is then subjected to a reducing treatment to obtain a catalyst composition of this invention. Instead of the evaporation treatment, a concentrating treatment may be used. For example, the product may be concentrated to about one-half of its original amount, and a solid is recovered from it by, for example, filtration and then treated similarly to the above to obtain the catalyst composition of this invention.

The evaporating treatment and the concentrating treatment may be carried out under atmospheric, reduced or elevated pressures. These treatments can be effected at room temperature or at elevated temperatures. The use of elevated temperatures, for example about 60° to about 90° C., is preferred.

The reducing treatment can be carried out in accordance with a known method by treating the resulting copper-containing silica gel with hydrogen at an elevated temperature. For example, the reducing treatment can be carried out by heat-treating the copper-containing silica gel with hydrogen at about 150° to about 500° C., preferably at about 200° to about 400° C., for about 1 to about 15 hours. Prior to the reducing treatment, the copper-containing silica gel may be preliminarily heat-treated. For example, the preliminary heat-treatment can be carried out by calcining it in the air at a temperature of about 400° to about 800° C., preferably about 500° to about 750° C., for about 1 to about 10 hours.

The copper content of the catalyst composition of this invention, in terms of the weight ratio of $SiO_2:Cu$, can be adjusted by properly selecting the amounts of the ammine complex of copper and the silica gel during the preparation of the catalyst composition. Preferably, the weight ratio of $SiO_2:Cu$ is from 1:about 0.001 to 1:about 2, more preferably from 1:about 0.01 to 1:about 1.

According to this invention, there is provided, in a process for producing ethylene glycol and/or a glycolic acid ester which comprises hydrogenating an oxalate diester in the gaseous or vapor phase at an elevated temperature in the presence of a hydrogenation catalyst, the improvement wherein the hydrogenation catalyst is the catalyst composition of the present invention composed of a reduction product of copper-containing silica gel formed by contacting an ammine complex of copper with silica gel having an average particle diameter of not more than $200\mu$. This process is carried out in a customary manner except that the specific catalyst composition of this invention is used. For example, it can be carried out by using the processes disclosed in Japanese Patent Publication No. 42971/1980 (corresponding to U.S. Pat. No. 4,112,245), German Pat. No. 459,603, and Japanese Laid-Open Patent Publication No. 40685/1980.

The starting oxalate diester used in the process of this invention is preferably a di($C_1$–$C_8$)alkyl ester of oxalic acid. Examples include dimethyl oxalate, diethyl oxalate, dibutyl oxalate and diamyl oxalate.

The reaction conditions in the presence of the catalyst composition of this invention can be properly selected in accordance with known methods. For example, preferred reaction conditions are as follows:

Reaction temperature

About 140° to about 300° C., preferably about 170° to about 260° C., more preferably about 180° to about 240° C.

Contact time (based on STP)

About 0.01 to about 20 seconds (about 0.02 to about 40 g.sec/ml), preferably about 0.2 to about 5 seconds (about 0.4 to about 10 g.sec/ml).

Reaction pressure

About 0.1 to about 200 atmospheres, preferably about 1 to about 40 atmospheres.

Mole ratio of hydrogen to oxalate diester

At least about 4, preferably about 10 to about 500.

The catalytic hydrogenation reaction of the oxalate diester can be carried out in any mode by contacting the oxalate diester with hydrogen gas and the catalyst composition in the gaseous or vapor phase in a fixed catalyst bed or a fluidized catalyst bed. The reaction can be performed either batchwise or continuously.

The hydrogenating catalyst of the invention does not contain chromium, as is apparent from the method of its preparation. Despite the fact that it does not contain chromium, the catalyst of the invention can efficiently catalyze a reaction of hydrogenating an oxalate diester to ethylene glycol and/or a glycolic acid ester, and the desired product can be obtained in a higher space time yield than in the case of using the known catalysts. Accordingly, the hydrogenating catalyst of this invention is particularly suitable for the industrial production of ethylene glycol and/or a glycolic acid ester from an oxalate diester.

By hydrogenating the oxalate diester in the presence of the hydrogenating catalyst composition of this invention, both ethylene glycol and a glycolic acid ester are generally formed. Ethylene glycol, or the glycolic acid ester, or both can be separated and recovered from the reaction products by any desired methods.

The following examples illustrate the present invention more specifically.

EXAMPLE 1

Cupric nitrate trihydrate [$Cu(NO_3)_2 \cdot 3H_2O$; 101.2 g] was dissolved in 300 ml of water, and 300 ml of concentrated aqueous ammonia was added to adjust the pH of the solution to about 11-12. Thus, a deep blue solution containing a copper-ammine complex was obtained. To the deep blue solution was added a suspension of 40 g of fine silica gel particles having an average particle diameter of 2.5μ (SYLOID 150, a product of Fuji-Davison Co., Ltd.) in 450 ml of water, and the mixture was stirred at room temperature for several hours.

Then, the temperature of the mixed solution was raised to about 85° to about 100° C. to evaporate most of the water. The residue was further dried at 120° C. for 12 hours. The dried product was washed fully with water, and dried again in air at 140° C. for 14 hours. The dried product was subjected to a reducing treatment at 350° C. for 2 to 3 hours to prepare a catalyst. The catalyst contained about 40% by weight of copper, and the weight ratio of copper to silicon dioxide was about 0.67.

EXAMPLE 2

1.4 ml of the catalyst prepared in Example 1 was filled in a stainless steel reaction tube having an inside diameter of 4 mm, and diethyl oxalate was catalytically hydrogenated at a reaction temperature of 215° C. and a pressure of 0.5 kg/cm$^2$.G with a contact time of 2.1 seconds. The mole ratio of hydrogen to diethyl oxalate fed to the reaction system was maintained at 45.

Analysis of the reaction product showed that the conversion of diethyl oxalate was 100%, the selectivity to ethylene glycol was 85.6%, and the selectivity to ethyl glycolate was 10.4%.

EXAMPLES 3 AND 4

Diethyl oxalate was catalytically hydrogenated under the same conditions as in Example 2 except that the reaction temperature and the mole ratio of hydrogen to diethyl oxalate were changed as shown in Table 1. The results are also shown in Table 1.

EXAMPLE 5

Cupric nitrate trihydrate (126.5 g) was dissolved in 300 ml of water, and 375 ml of concentrated aqueous ammonia was added to adjust the pH of the solution to about 11-12. Thus, a deep blue solution of a copper-ammine complex was obtained. To the deep blue solution was added a suspension of 100 g of fine silica gel particles having an average particle diameter of 4 microns (SYLOID 65, a product of Fuji-Davison Co., Ltd.) in 500 ml of distilled water, and the mixture was stirred at room temperature for several hours. The mixed solution was then heated to about 90° to about 100° C. to evaporate most of the water, and further dried at 120° C. for 12 hours. The dried product was thoroughly washed with water, and again dried at 140° C. for 14 hours. The dried product was subjected to a reducing treatment in a stream of hydrogen at 350° C. for 2 hours to prepare a catalyst. The catalyst contained about 20% by weight of copper, and the weight ratio of copper to silicon dioxide was about 0.25.

EXAMPLE 6

1.4 ml of the catalyst prepared in Example 5 was filled in a stainless steel reaction tube having an inside diameter of 4 mm, and diethyl oxalate was catalytically hydrogenated at a reaction temperature of 235° C. and a pressure of 0.5 kg/cm$^2$.G with a contact time of 2.1 seconds. The mole ratio of hydrogen to diethyl oxalate fed into the reaction system was maintained at 45.

Analysis of the reaction product showed that the conversion of diethyl oxalate was 81.1%, the selectivity to ethylene glycol was 57.0%, and the selectivity to ethyl glycolate was 44.3%.

EXAMPLE 7

Cupric nitrate trihydrate (253 g) was dissolved in 750 ml of water, and 750 ml of concentrated aqueous ammonia was added to adjust the pH of the solution to about 11-12. Thus, a deep blue solution containing a copper-ammine complex was obtained. To the deep blue solution was added a suspension of 100 g of ultrafine silica gel particles having an average particle diameter of 10 to 20 mμ in 1000 ml of water, and the mixture was stirred at room temperature for several hours.

Then, the mixed solution was heated to about 85° to about 100° C. to evaporate most of the water, and further dried at 120° C. for 16 hours. The dried product was fully washed with water, and again dried at 120° C. for 24 hours. The dried product was subjected to a reducing treatment in a stream of hydrogen at 200° C. for 12 hours to prepare a catalyst. The catalyst contained about 40% by weight of copper, and the weight ratio of copper to silicon dioxide was about 0.67.

EXAMPLES 8 TO 11

1.4 ml of the catalyst prepared in Example 7 was filled in a stainless steel reaction tube having an inside diameter of 4 mm, and diethyl oxalate was catalytically hydrogenated at a pressure of 0.5 kg/cm$^2$.G with a contact time of 2.1 seconds. The reaction temperatures and the mole ratios of hydrogen to the starting diethyl oxalate are shown in Table 2. The results are also shown in Table 2.

TABLE 1

| Example | Reaction temperature (°C.) | Mole ratio of hydrogen to diethyl oxalate | Conversion of diethyl oxalate (%) | Selectivity to ethylene glycol (%) | Selectivity to ethyl glycolate (%) |
| --- | --- | --- | --- | --- | --- |
| 3 | 215 | 11 | 67.4 | 58.6 | 37.5 |
| 4 | 235 | 11 | 92.8 | 68.9 | 28.4 |

TABLE 2

| Example | Reaction temperature (°C.) | Mole ratio of hydrogen to diethyl oxalate | Conversion of diethyl oxalate (%) | Selectivity to ethylene glycol (%) | Selectivity to ethyl glycolate (%) |
|---|---|---|---|---|---|
| 8 | 205 | 45 | 100 | 92.8 | 1.4 |
| 9 | 205 | 11 | 82.0 | 63.7 | 32.7 |
| 10 | 215 | 11 | 94.7 | 69.0 | 27.1 |
| 11 | 220 | 11 | 100 | 93.1 | 2.5 |

EXAMPLE 12

Cupric nitrate trihydrate (50 g) was dissolved in 150 ml of water, and 200 ml of concentrated aqueous ammonia was added to adjust the pH of the solution to about 11-12. Thus, a deep blue solution containing a copper-ammine complex was obtained. To the deep blue solution was added 19.2 g of fine silica gel particles having an average particle diameter of 100 microns, and the mixture was stirred at room temperature for several hours.

Then, the mixture was heated to about 85° C. to about 100° C. to evaporate most of the water, and further dried at 120° C. for 16 hours. The dried product was thoroughly washed with water, again dried at 120° C. for 24 hours, and subjected to a reducing treatment in a stream of hydrogen at 200° C. for 12 hours to prepare a catalyst. The catalyst contained about 40% by weight of copper, and the weight ratio of copper to silicon dioxide was about 0.67.

EXAMPLES 13 AND 14

1.4 ml of the catalyst prepared in Example 12 was filled in a stainless steel reaction tube having an inside diameter of 4 mm, and diethyl oxalate was catalytically hydrogenated at a pressure of 0.5 kg/cm$^2$.G with a contact time of 2.1 seconds. The reaction temperatures were as indicated in Table 3. The results are shown in Table 3.

TABLE 3

| Example | Reaction temperature (°C.) | Mole ratio of hydrogen to diethyl oxalate | Conversion of diethyl oxalate (%) | Selectivity to ethylene glycol (%) | Selectivity to ethyl glycolate (%) |
|---|---|---|---|---|---|
| 13 | 200 | 45 | 80.4 | 51.9 | 46.2 |
| 14 | 215 | 45 | 100 | 93.1 | 4.6 |

COMPARATIVE EXAMPLE 1

A catalyst was prepared in the same way as in Example 12 except that 19.2 g of silica gel having an average particle diameter of 250 microns was used instead of silica gel having an average particle diameter of 100 microns. The catalyst contained about 40% by weight of copper, and the weight ratio of copper to silicon dioxide was about 0.67.

COMPARATIVE EXAMPLES 2 TO 4

1.4 ml of the catalyst prepared in Comparative Example 1 was filled in a stainless steel reaction tube having an inside diameter of 4 mm, and diethyl oxalate was catalytically hydrogenated at a reaction pressure of 0.5 kg/cm$^2$.G with a contact time of 2.3 seconds. The reaction temperature and the mole ratio of hydrogen to diethyl oxalate were changed as shown in Table 2. The results are also shown in Table 4.

TABLE 4

| Comparative Example | Reaction temperature (°C.) | Mole ratio of hydrogen to diethyl oxalate | Conversion of diethyl oxalate (%) | Selectivity to ethylene glycol (%) | Selectivity to ethyl glycolate (%) |
|---|---|---|---|---|---|
| 2 | 200 | 45 | 9.6 | ~0 | 84.7 |
| 3 | 215 | 45 | 54.3 | ~0 | 29.3 |
| 4 | 235 | 11 | 52.1 | 7.6 | 25.7 |

EXAMPLE 15

The dried product prepared as in Example 1 (the dried product before the reducing treatment) was molded into pellets having a size of 4 mm×4 mmφ, and calcined in air at about 750° C. for 5 hours. The calcined product was crushed and screened into a size of 9 to 16 mesh, and subjected to a reducing treatment in a stream of hydrogen at about 200° C. for 5 hours to prepare a catalyst. The catalyst contained about 40% by weight of copper, and the weight ratio of copper to silicon dioxide was about 0.67.

EXAMPLE 16

Twenty-five milliliters of the catalyst prepared in Example 15 was filled in a stainless steel reaction tube having an inside diameter of 19.4 mm and a length of 700 mm, and dimethyl oxalate was catalytically hydrogenated at a reaction temperature of 200° C., a space velocity (SV) of 6500 hr$^{-1}$, a liquid hourly space velocity (LHSV) of 0.66 g/ml.hr, and a reaction pressure of 20 kg/cm$^2$.G. The mole ratio of hydrogen to dimethyl oxalate fed into the reaction system was maintained at 40.

Analysis of the reaction product showed that the conversion of dimethyl oxalate was 100%, the selectivity to ethylene glycol was 96.8%, and the selectivity to methyl glycolate was 0.9%.

What we claim is:

1. A hydrogenation catalyst composition for use in the hydrogenation of an oxalate diester, said composition being composed of a reduction product of copper-containing silica gel formed by contacting an amine complex of copper with silica gel having an average particle diameter of not more than 200μ.

2. The composition of claim 1 wherein the weight ratio of SiO$_2$ to Cu is from 1:about 0.001 to 1:about 2.

3. A process for producing a hydrogenation catalyst composition for use in the hydrogenation of oxalate diester, which comprises contacting an amine complex of copper with silica gel having an average particle diameter of not more than 200μ in the presence of an aqueous medium, and subjecting the resulting copper-containing silica gel to a reducing treatment.

4. The process of claim 3 wherein the contacting is carried out at room temperature to about 150° C.

5. The process of claim 3 wherein the reducing treatment is carried out in the presence of hydrogen at a temperature of about 150° to about 500° C.

* * * * *